(12) United States Patent
Okuyama et al.

(10) Patent No.: US 7,197,924 B2
(45) Date of Patent: Apr. 3, 2007

(54) APPARATUS AND METHOD FOR EVALUATING SUBTERRANEAN ENVIRONMENTS

(75) Inventors: Keita Okuyama, Hitachi (JP); Kenji Noshita, Hitachi (JP); Akira Sasahira, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 143 days.

(21) Appl. No.: 11/114,132

(22) Filed: Apr. 26, 2005

(65) Prior Publication Data
US 2006/0053877 A1    Mar. 16, 2006

(30) Foreign Application Priority Data
Apr. 27, 2004    (JP)    ............................. 2004-130946

(51) Int. Cl.
*E21B 49/08*    (2006.01)
(52) U.S. Cl. ................................ 73/152.42; 73/152.41
(58) Field of Classification Search ..................... None
See application file for complete search history.

(56) References Cited

U.S. PATENT DOCUMENTS 6,779,384 B2 *   8/2004   Chun ............................. 73/38

FOREIGN PATENT DOCUMENTS

| JP | 06-130158 | 5/1994 |
|---|---|---|
| JP | 09-061540 | 7/1997 |
| JP | 09-211146 | 8/1997 |
| JP | 2000-337070 | 5/2000 |
| JP | 2000-178956 | 6/2000 |
| JP | 2000-514181 | 10/2000 |
| JP | 2000-314289 | 11/2000 |
| JP | 2003-014876 | 1/2003 |
| JP | 2003-165585 | 6/2003 |
| JP | 2004-011139 | 1/2004 |

* cited by examiner

*Primary Examiner*—Hezron Williams
*Assistant Examiner*—Paul M. West
(74) *Attorney, Agent, or Firm*—Dickstein Shapiro LLP

(57) ABSTRACT

A subterranean environment evaluating apparatus and method, which measure, e.g., the geologic distribution coefficient in a subterranean environments using, e.g., a pit formed by boring. The subterranean environment evaluating apparatus comprises a geologic evaluation sensor, a pump, an analyzer, a PC, a data transmitter, etc., and it is disposed in the pit formed underground by boring. The geologic evaluation sensor is disposed to form a thin layer channel defined by the surface of a rock bed. Groundwater mixed with a tracer is caused to flow through the sensor, and the analyzer measures a change of tracer concentration in the groundwater between before and after contact of the groundwater with the rock bed. The PC determines a breakthrough curve from the change of tracer concentration, thereby calculating the distribution coefficient (Kd) between the rock bed and the groundwater and the effective diffusion coefficient of the rock bed.

9 Claims, 6 Drawing Sheets

APPARATUS AND METHOD FOR EVALUATING SUBTERRANEAN ENVIRONMENTS

BACKGROUND OF THE INVENTION

1. Field of the Invention

The present invention relates to an apparatus and method for evaluating subterranean environments to select a site for installation of a geologic depository facility of radioactive wastes and to evaluate the behaviors of waste materials and/or the performance of artificial barriers for geologic depository.

2. Description of the Related Art

Geologic depository has been studied as a method for treating high-level radioactive wastes (HLW) prepared by melting and solidifying glass materials in which waste liquids discarded from a nuclear reactor, etc. are sealed off, and various assessments have been made regarding safety of geologic depository. The term "geologic depository" means a disposal method of burying high-level radioactive wastes, of which decay heat has been suppressed to some extent, in a rock bed at a depth of 300 m or more, and storing them for a very long period in a condition isolated from zones of life.

Safety is the most important assessment item when selecting a site for construction of a geologic depository facility and specifications of the geologic depository facility. In other words, it is required to evaluate possibilities of migration of radionuclides by groundwater, etc. and migration to other types of nuclides, and to select the site and specifications so that radiation doses in the zones of life meet safety standards for a long future period.

The safety assessment is performed as follows. Various scenarios (such as a groundwater scenario and an approach scenario) are set for time-dependent changes of the high-level radioactive wastes buried deeply underground, and mathematical models for describing those scenarios are constructed. Various parameters (actually measured values and assumed values) affecting the migrations of nuclides are entered in the mathematical models to make computer simulation based on a great deal of computations, thereby determining the time-dependent changes of radiation doses in the zones of life.

There are various parameters for use in the safety assessment simulation. Examples of those parameters include ones characterizing chemical properties, such as the distribution coefficient (Kd) of a radionuclide in groundwater with respect to rock, the pH-value of the groundwater, the oxidation/reduction potentials of the groundwater, and the zeta potential of the groundwater, and others characterizing physical properties, such as the diffusion coefficient of rock, the water permeability coefficient of rock, and the temperature of the groundwater.

To measure those parameters, a rock sample and a groundwater sample must be obtained. According to a known method, for example, a pit is formed underground by boring. A rock sample and a groundwater sample are obtained from the pit and taken into a glove box installed in an experiment facility on the ground. Then, tests for measuring the parameters are performed in the glove box. A space in the glove box is adjusted to match with the atmospheric atmosphere in the underground pit from which the rock sample and the groundwater sample were obtained.

SUMMARY OF THE INVENTION

Because the atmospheric pressure in the underground differs from that on the ground, the types of elements dissolved in groundwater and the amount of the dissolved elements are changed, and microorganisms exist in the underground. Further, an oxygen concentration of an atmosphere is lower in the underground than on the ground, and a reducing atmosphere exists in the underground. Therefore, when the rock sample and the groundwater sample are separated from the original subterranean environments, there is a possibility that those samples are deteriorated to cause some effects on the parameters.

Also, the rock sample and the groundwater sample both obtained from the underground pit tend to often denature with mixing of foreign matters, such as cutting oil, during the sampling process. Accordingly, tests conducted in the glove box installed in the laboratory facility on the ground have a difficulty in accurately determining the parameters for the migrations of nuclides.

For that reason, there is demanded a method of measuring parameters, which characterizes the geologic properties, in the subterranean environments without separating the rock sample and the groundwater sample from the original environments. However, a satisfactory method is not yet found up to now.

Meanwhile, the inventors have previously proposed a small reaction device for solid-liquid interface reactions (Japanese Patent Application No. 2003-165585) as means for evaluating a phenomenon occurred at the interface between a solid, such as a rock bed, and a liquid, such as groundwater, when the solid and the liquid are brought into contact with each other.

The proposed device comprises a board provided with an inlet and an outlet for a reaction solution, and a gasket being thinner than the board and having a slit at the center thereof. The board, the gasket, and a solid specimen causing an interface reaction with a liquid phase of the reaction solution are set a multilayered state and an external pressure is applied to them. The board, the gasket, and the specimen are thereby closely contacted with each other to form a reaction channel by the slit in the gasket and the solids facing an opening of the slit. In such a state, the reaction solution is introduced to flow into the reaction channel through the inlet, and the reaction solution having passed the reaction channel is discharged through the outlet.

That construction provides a small reaction device for solid-liquid interface reactions capable of preventing a liquid leakage from the reaction channel having a very thin thickness, and various solid-liquid interface reactions can be measured with high accuracy by measuring the solid-liquid interface reactions in environments close to actual ones.

In view of the above-mentioned problem that the subterranean environments cannot be precisely reproduced in a facility on the ground, it is an object of the present invention to provide an apparatus and method for evaluating subterranean environments, which can accurately measure solid-liquid interface reactions in subterranean environments by applying the previously proposed small reaction device for solid-liquid interface reactions to the actual subterranean environments.

To achieve the above object, the present invention provides a subterranean environment evaluating apparatus for measuring a diffusion coefficient of rock and a distribution coefficient between rock and groundwater by using the groundwater and a rock bed in subterranean environments, wherein the apparatus comprises a thin layer channel formed in a subterranean structure for allowing the groundwater to pass through the thin layer channel; and a concentration analyzer for measuring a concentration change of groundwater composition between an inlet and an outlet of the thin layer channel when the groundwater is caused to pass through said the layer channel.

The thin layer channel is constituted as a three-layered geologic evaluation sensor comprising a board chip having an inlet and an outlet for a solution, a gasket made of an elastic material and having a slit formed therein to provide a part of a reaction channel in the form of a reaction cell serving also as a channel, and a specimen as a measurement target. Also, the thin layer channel is constituted using, as the specimen, a rock bed surface of the subterranean structure.

Stated another way, a base for the above-mentioned small reaction device for solid-liquid interface reactions is prepared in a pit formed underground by boring from on the ground or a shallow hole formed in a rock bed defining a space for a subterranean laboratory facility. The gasket and the board chip are successively overlaid on the base to constitute the geologic evaluation sensor. The subterranean environment evaluating apparatus further comprises a pump, an analyzer, a data transmitter, etc., and it is disposed underground. Therefore, the distribution coefficient (Kd) between the rock bed and the groundwater and the diffusion coefficient of the rock bed can be accurately measured in subterranean environments without separating a rock sample and a groundwater sample from the original environments.

According to another aspect, a rock projection is left at the bottom of a subterranean structure. The geologic evaluation sensor constituted using, as the specimen, the rock projecting is disposed on one side of the rock projection. On the other side of the rock projection, a container containing a solution prepared by mixing a tracer in the groundwater is disposed such that its one side is defined by the rock projection. The geologic evaluation sensor measures the solution diffusing from the container through the rock projection, thereby determining the diffusion coefficient and the distribution coefficient from a measured concentration change of the solution. With this aspect, a subterranean environment evaluating apparatus with high sensitivity can be provided.

A subterranean environment evaluating method of the present invention comprises the steps of causing groundwater to flow through a thin layer channel formed by using a rock bed surface as a part of the thin layer channel; measuring a concentration change of groundwater composition between an inlet and an outlet of the thin layer channel to obtain a breakthrough curve; and determining the diffusion coefficient and the distribution coefficient based on the breakthrough curve.

According to the present invention, it is possible to accurately evaluate the nuclide confining capability of geologic environments.

DESCRIPTION OF THE PREFERRED EMBODIMENTS

The construction of a subterranean environment evaluating apparatus according to a first embodiment of the present invention will be described below with reference to FIGS. 1 to 4.

Figure 1:
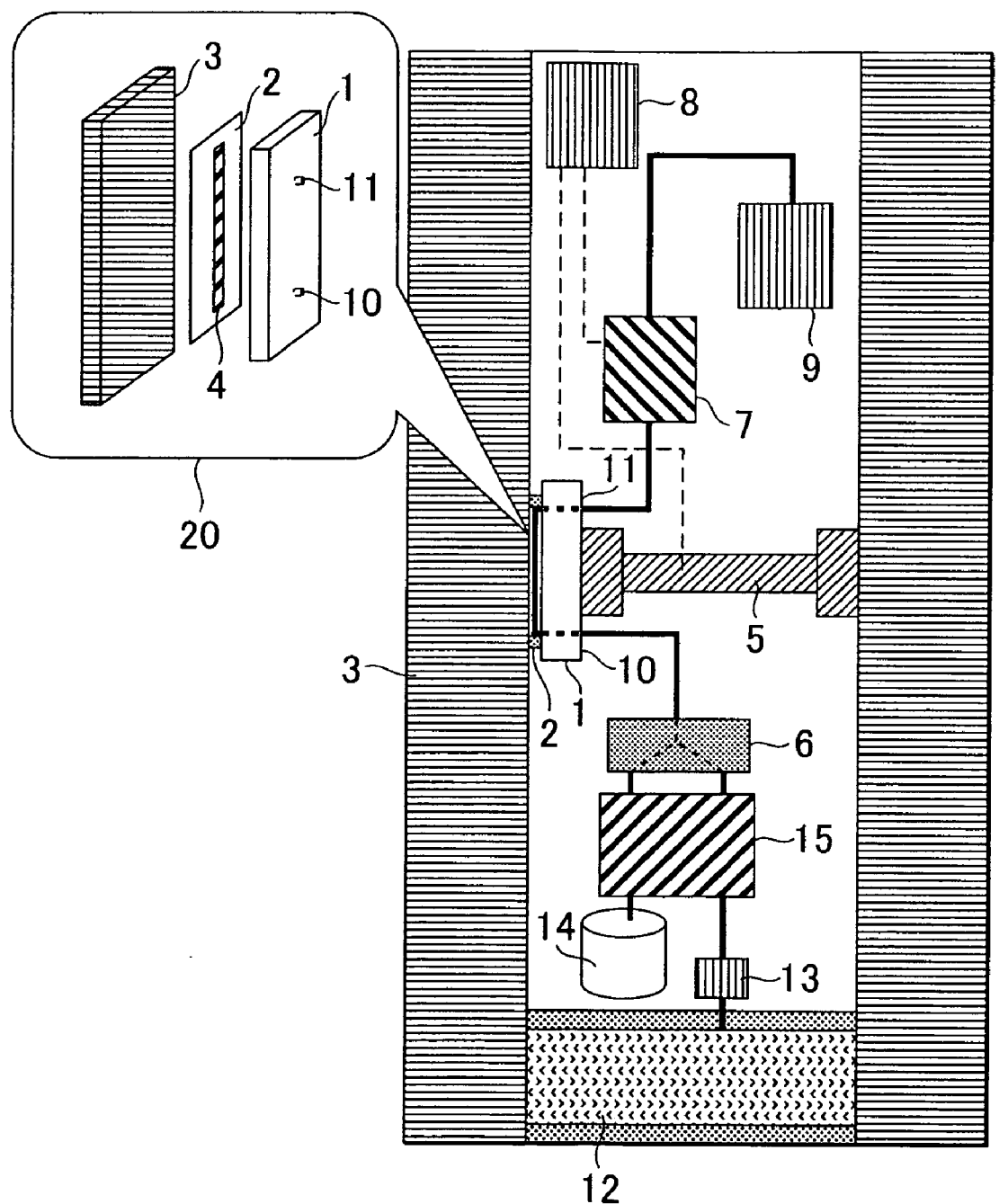
FIG. 1 is a schematic view showing the construction of a subterranean environment evaluating apparatus according to a first embodiment of the present invention.

FIG. 1 is a schematic view showing the construction of the subterranean environment evaluating apparatus according to the first embodiment of the present invention. The subterranean environment evaluating apparatus is disposed on a rock bed (specimen) 3 defining an inner surface of a pit formed underground by boring.

The subterranean environment evaluating apparatus comprises a board chip 1, a gasket 2, the specimen 3, a reaction cell 4 serving also as a channel, a pressure applying device 5, a liquid feed pump 6, a nuclide concentration analyzer 7, a PC (Personal Computer) 8, a solution reservoir 9, an inlet 10, and an outlet 11. The subterranean environment evaluating apparatus further comprises a groundwater pool 12 for storing groundwater seeping through the rock bed, a device 13 for taking in the groundwater from the groundwater pool 12, and a tracer mixing unit 15 for mixing a proper amount of a tracer 14 into the taken-in groundwater. Though not shown, a data transmitter for transmitting and receiving data with respect to a facility on the ground via the PC 8, etc. are also provided.

The board chip 1 is made of polytetrafluoroethylene (PTFE) and has dimensions of, e.g., 60 mm length, 25 mm width, and 10 mm thickness. The board chip 1 has the inlet 10 and the outlet 11 for allowing passage of a fluid, which are formed as holes penetrating through the board chip 1 in the direction of thickness. Each of the inlet 10 and the outlet 11 has a diameter of, e.g., 0.5 mmφ.

The gasket 2 is made of an elastic material, for example, polytetrafluoroethylene (PTFE), i.e., the same material as the board chip 1, and has dimensions of, e.g., 60 mm length, 25 mm width, and 160 μm thickness. A slit serving as a part of a reaction channel is formed in a central area of the gasket 2. The slit has dimensions of, e.g., 20 mm length, 2 mm width, and 160 μm thickness.

The specimen 3 is given as a wall surface of the rock bed defining an inner space of the pit formed by, e.g., boring. The bored bit has dimensions of, e.g., 100 mm diameter and 500 m depth. A part of the surface of the specimen 3, which contacts with the gasket 2, is polished to be flat by using, e.g., a #220-file. Although the specimen surface is polished by using the file or the like, minute irregularities remain on the specimen surface.

The board chip 1, the gasket 2, and the specimen (rock bed) 3 are arranged in a successively overlaid state, and an external force is applied to them from the pressure applying device 5. Correspondingly, the gasket 2 is elastically deformed in following relation to the surface irregularities of the specimen 3 and is brought into close contact with the specimen 3, i.e., the rock bed, thereby constituting a geologic evaluation sensor. The slit in the gasket 2, a part of the surface of the board chip 1, and a part of the surface of the specimen 3 cooperatively form a reaction channel used for the geologic evaluation sensor, i.e., the reaction cell 4 serving also as the channel. In this way, a part of the specimen 3 in the solid phase constitutes a part of a thin liquid channel wall.

The reaction cell 4 serving also as the channel are constituted as an assembly in which the board chip 1, the gasket 2, and the specimen (rock bed) 3 are successively overlaid and closely contacted with each other under application of an external force. The liquid feed pump 6 is connected to the inlet 10 of the board chip 1, and the nuclide concentration analyzer (split sampling unit) 7 is connected to the outlet 11 of the board chip 1.

The pressure applying device 5 is, for example, an electromagnetic clamp and is used to apply an external force to the successively overlaid assembly of the board chip 1, the gasket 2, and the specimen 3. One of opposite extending and contracting surfaces of the pressure applying device 5 is held abutted against the successively overlaid assembly of the board chip 1, the gasket 2, and the specimen 3, while the other extending and contracting surface is held abutted against, e.g., the surface of the rock bed positioned just opposing to the specimen 3. The operation of extending and contracting the pressure applying device 5 can be controlled from the PC 8.

Instead of the above-described electromagnetic clamp, a hydraulic clamp or a water-hydraulic clamp, for example, may also be used to apply an external force to the successively overlaid assembly of the board chip 1, the gasket 2, and the specimen 3.

With the geologic evaluation sensor of this embodiment, an interaction between a part of materials contained in the specimen 3 and a material dissolved in a solution occurs upon contact of the solution with the specimen 3, i.e., the rock bed. The interaction is caused in such a process that a tracer material in the solution is diffused into the specimen 3, is adsorbed on the specimen surface, or forms colloid in the solution under influences from the materials contained in the specimen. By measuring a change of tracer concentration in the solution between before and after contact of the solution with the specimen 3, it is possible to obtain the distribution coefficients (Kd) of the rock bed and the nuclide, and the effective diffusion distribution coefficient of the rock bed.

Figure 2:
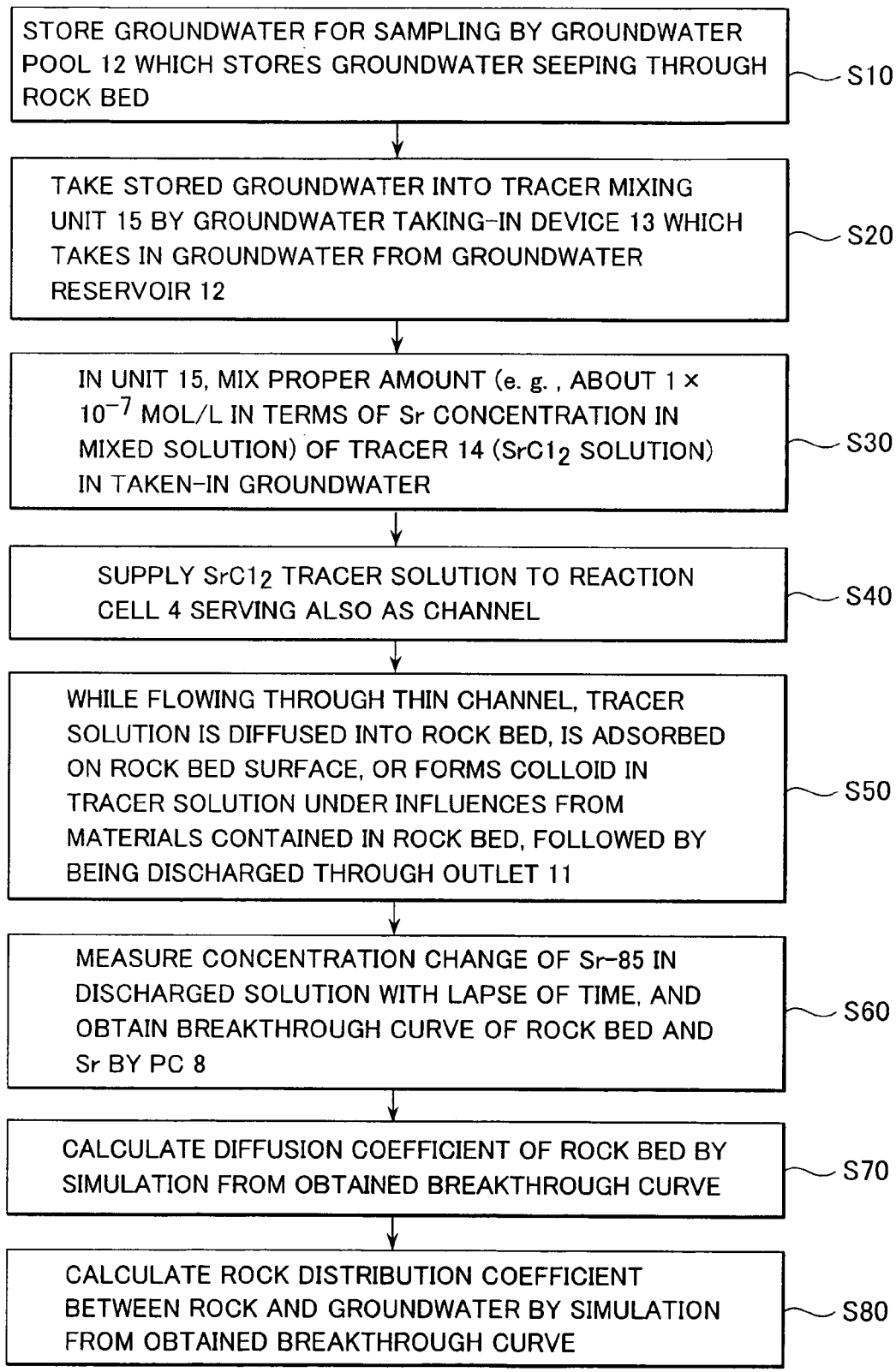
FIG. 2 is a flowchart of a subterranean environment evaluating method according to the first embodiment of the present invention.

FIG. 2 is a flowchart showing test procedures. The test procedures are processed by a program installed in the PC 8. First, groundwater seeping through the rock bed is stored in a groundwater pool 12 for sampling (S10). Then, the sampled groundwater is taken into the tracer mixing unit 15 by the device 13 for taking in the groundwater from the groundwater pool 12 (S20). In the tracer mixing unit 15, a proper amount (e.g., about $1\times10^{-7}$ mol/L in terms of Sr concentration in a mixed solution) of the tracer 14 ($SrCl_2$ solution) is mixed in the taken-in groundwater (S30).

Thereafter, the tracer solution containing $SrCl_2$ as a radioactive material is supplied to the reaction cell 4 serving also as the channel (S40). While flowing through the thin channel, the tracer solution is diffused into the rock bed, is adsorbed on the rock bed surface, or forms colloid in the tracer solution under influences from the materials contained in the rock bed, followed by being discharged through the outlet 11 (S50).

The discharged solution is measured for a concentration change of Sr-85 in the solution with the lapse of time, and a breakthrough curve of the rock bed and Sr is obtained by the PC 8 (S60). From the obtained breakthrough curve, the diffusion coefficient of the rock bed is calculated by simulation (S70). Further, from the obtained breakthrough curve, the rock distribution coefficient between rock and groundwater is calculated by simulation (S80).

The foregoing measurement process will be described in more detail below. The subterranean environment evaluating apparatus according to the first embodiment, shown in FIG. 1, is a test apparatus for measuring changes of $Sr^{2+}$ ions in the $SrCl_2$ solution caused by the adsorption and dissociation reactions of $Sr^{2+}$ ions in the $SrCl_2$ solution with respect to the wall surface of the rock bed, i.e., the specimen 3, in the bored pit, and by the diffusion of $Sr^{2+}$ ions into the rock bed.

The $SrCl_2$ solution fed by the liquid feed pump 6 is supplied through the fluid inlet 10 to the reaction cell 4 serving also as the channel. While flowing through the thin channel formed on the specimen 3, the $SrCl_2$ solution is diffused into the specimen 3, i.e., the rock bed, is adsorbed on the rock bed surface, or forms colloid in the tracer solution under influences from the materials contained in the specimen 3, followed by being discharged through the outlet 11. The discharged solution is measured for a concentration change of Sr-85 in the solution with the lapse of time by the nuclide concentration analyzer 7, and the measured data is sent to the PC 8. The PC 8 processes the data to obtain a breakthrough curve of the rock bed and Sr. The solution having been subjected to the measurement of the nuclide concentration by the nuclide concentration analyzer 7 is sent to solution reservoir 9 and is stored therein for a measurement period.

In the above-described embodiment, the nuclide concentration analyzer 7, the PC 8, and the solution reservoir 9 are disposed underground together with the geologic evaluation sensor. As one of modifications, the nuclide concentration analyzer 7, the PC 8, and the solution reservoir 9 may be disposed on the ground, and the solution, etc. discharged from the geologic evaluation sensor disposed underground may be fed to the nuclide concentration analyzer 7 on the ground.

The tracer 14 mixed into the groundwater taken in by the taking-in device 13 from the groundwater pool 12, which stores the groundwater seeping through the rock bed, is an isotope element of the radionuclide contained in radioactive wastes. Practical examples of the tracer 14 are ions or colloids of Cs, Sr, Ra, Co, Ni, Pb, Sm, Eu, Ac, Am, Cm, Pb, Zr, Nb, Tc, Mo, Sn, Pa, Th, U, Np, Pu, Cl, I, Se, and C. Other examples are ions or colloids showing similar migrations to those of the above elements, or fluorescent ions or fluorescent colloids showing similar migrations to those of the above elements.

Figure 3:
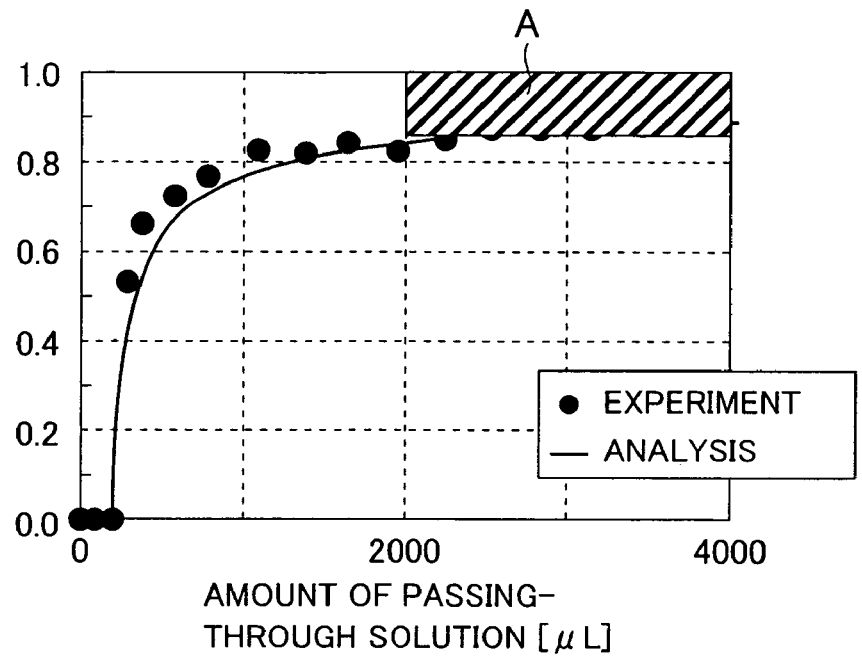
FIG. 3 is a characteristic graph showing one example of a breakthrough curve obtained by a geologic evaluation sensor.

FIG. 3 shows a breakthrough curve obtained with the geologic evaluation sensor. A description is now made of a manner for calculating the rock diffusion coefficient between rock and groundwater from the obtained breakthrough curve. The plotted example is the breakthrough curve obtained by using, as the rock sample, granite produced in Inada (one district in Japan) and, as the groundwater sample, a solution containing H-3 mixed as a tracer in the groundwater. A black circle indicates an experimental value, and a solid line indicates an analysis result.

The vertical axis of the breakthrough curve represents a ratio of the H-3 concentration at the outlet 11 of the geologic evaluation sensor to the H-3 concentration at the inlet 10 thereof, and the horizontal axis represents the amount of the passing-through H-3 solution. H-3 is an isotope of H and has exactly the same properties except for emitting radiations.

For that reason, H-3 is used as a tracer for motions of water. A flow rate of the passing-through H-3 solution is 6 μL/min.

The board chip 1 has dimensions of 40 mm length, 25 mm width, and 10 mm thickness. The gasket 2 has dimensions of 40 mm length, 25 mm width, and 160 μm thickness. The Inada granite as the rock sample (i.e., the specimen 3) has dimensions of 40 mm length, 25 mm width, and 10 mm thickness. The surface of the rock sample is polished by using a #220-file. The slit has dimensions of 20 mm length, 4 mm width, and 160 μm thickness.

The breakthrough curve will be described below. As soon as the H-3 solution is passed through the geologic evaluation sensor, the H-3 concentration starts to rise at the outlet 11 of the sensor. With the continued passing-through of the H-3 solution, however, the ratio of the H-3 concentration at the outlet 11 to the H-3 concentration at the inlet 10 will not be 1. As indicated by a hatched area A, the H-3 concentration at the outlet 11 is lower than the H-3 concentration at the inlet 10.

The reason is that when the H-3 solution flows through the reaction cell 4 serving also as the channel and contacts with the specimen 3, H-3 is diffused into the specimen and the H-3 amount in the H-3 solution flowing through the reaction cell 4 serving also as the channel is reduced. This point can be understood from simulation studies based on a two-dimensional advection diffusion model. As a result of the simulation studies made on the breakthrough curve shown in FIG. 3, the diffusion coefficient of the Inada granite was calculated as $6 \times 10^{-12}$ m$^2$/s.

The term "two-dimensional advection diffusion equation" is constructed by modeling an advection field based on the Navier-Stokes equations and a diffusion field based on the Darcy equation, respectively, and applying the resulting models to a two-dimensional field of rock and groundwater in the form of simultaneous equations. For more details, see, e.g., Takahiko Tanahashi, "CFD-Advection Diffusion Equation for Beginners", Corona Publishing Co., Ltd. (published Oct. 15, 1996).

A description is now made of a manner for calculating the rock distribution coefficient between rock and groundwater from a breakthrough curve obtained with the geologic evaluation sensor.

Figure 4:
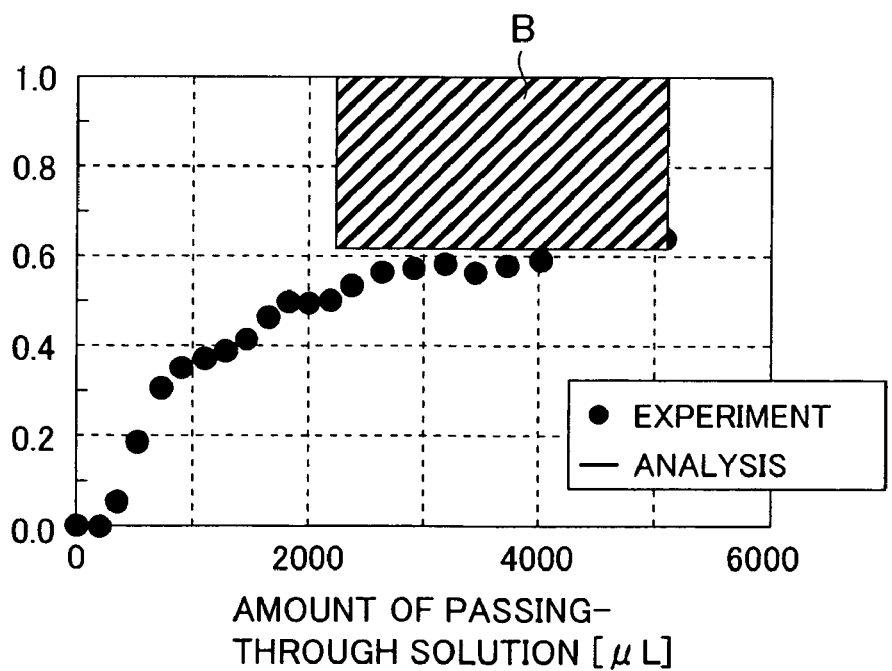
FIG. 4 is a characteristic graph showing another example of the breakthrough curve obtained by the geologic evaluation sensor.

FIG. 4 shows a breakthrough curve obtained by using, as the rock sample, the Inada granite and, as the groundwater sample, a SrCl$_2$ solution. The vertical axis of the breakthrough curve represents a ratio of the Sr$^{2+}$ concentration at the outlet 11 of the geologic evaluation sensor to the Sr$^{2+}$ concentration at the inlet 10 thereof, and the horizontal axis represents the amount of the passing-through SrCl$_2$ solution. The SrCl$_2$ solution has the Sr concentration of $1 \times 10^{-7}$ mol/L and pH=8. A flow rate of the passing-through SrCl$_2$ solution is 3 μL/min.

The board chip 1 has dimensions of 40 mm length, 25 mm width, and 10 mm thickness. The gasket 2 has dimensions of 40 mm length, 25 mm width, and 160 μm thickness. The Inada granite as the rock sample (i.e., the specimen 3) has dimensions of 40 mm length, 25 mm width, and 10 mm thickness. The surface of the rock sample is polished by using a #220-file. The slit has dimensions of 20 mm length, 2 mm width, and 160 μm thickness.

The breakthrough curve shown in FIG. 4 will be described below. As soon as the Sr-85 solution is passed through the geologic evaluation sensor, the Sr$^{2+}$ concentration starts to rise at the outlet 11 of the sensor. With the continued passing-through of the SrCl$_2$ solution, however, the ratio of the Sr$^{2+}$ concentration at the outlet 11 of the geologic evaluation sensor to the Sr$^{2+}$ concentration at the inlet 10 will not be 1 (as indicated by a hatched area B in FIG. 4). Namely, the Sr$^{2+}$ concentration at the outlet 11 is lower than the Sr$^{2+}$ concentration at the inlet 10.

Also, from comparison between the hatched area A in FIG. 3 and the hatched area B in FIG. 4, it is understood that the Sr$^{2+}$ concentration at the inlet 10 is lower than the H-3 concentration at the inlet 10. The reason is that when the Sr$^{2+}$ solution flows through the reaction cell 4 serving also as the channel and contacts with the specimen (rock bed) 3, Sr$^{2+}$ is diffused into the rock bed and is adsorbed to the specimen materials in the rock bed, whereby the Sr$^{2+}$ amount in the SrCl$_2$ solution flowing through the reaction cell 4 serving also as the channel is reduced.

That point can also be understood from simulation studies based on a two-dimensional advection diffusion model. As a result of the simulation studies made on the breakthrough curve shown in FIG. 4, the distribution coefficient of the Inada granite—Sr was calculated as $1 \times 10^{-2}$ m$^3$/kg.

In the above description, the depth of the reaction channel (i.e., the thickness of the gasket 2) is set to 160 μm. The depth of the reaction channel is selected depending on the properties of the test target (such as the effective diffusion coefficient and the rates of adsorption and dissociation reactions of Sr$^{2+}$ ions with respect to the rock bed) and the solid-liquid reaction (rock bed and Sr) as a target. In practical applications, the depth of the reaction channel is, e.g., in the range of about 50 to 200 μm, and the length of the reaction channel is, e.g., in the range of about 20 to 100 mm. Instead of the SrCl$_2$ solution, a NiCl$_2$ solution, a CsCl$_2$ solution or the like is also usable as the reaction solution.

Figure 5:
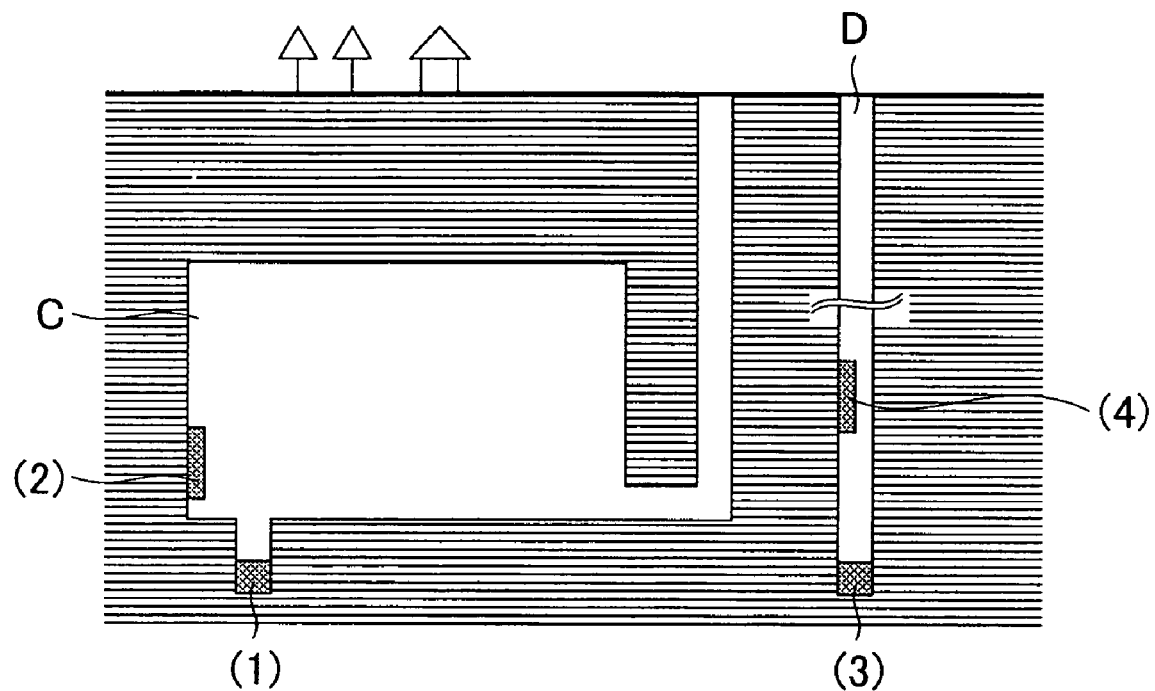
FIG. 5 is an explanatory view showing one example of application of the geologic evaluation sensor.

FIG. 5 shows various application examples of the geologic (environment) evaluation sensor according to the present invention. In FIG. 5, C represents a laboratory facility constructed underground, and a shallow hole is formed in a rock bed at the bottom of the laboratory facility. Then, as indicated by (1), a geologic environment evaluation sensor is buried in the hole to measure the distribution coefficient (Kd) between a rock bed and ground water and the diffusion coefficient of the rock bed. Alternatively, as indicated by (2), the geologic environment evaluation sensor may be disposed on the rock bed defining a wall of the laboratory facility.

In FIG. 5, D represents a pit formed by boring in a site candidate for waste depository. The distribution coefficient (Kd) between the rock bed and ground water and the diffusion coefficient of the rock bed are measured by burying the geologic environment evaluation sensor in the rock bed at the bottom (3) of the pit or in an intermediate inner wall surface (4) of the pit in the direction of depth.

Figure 6:
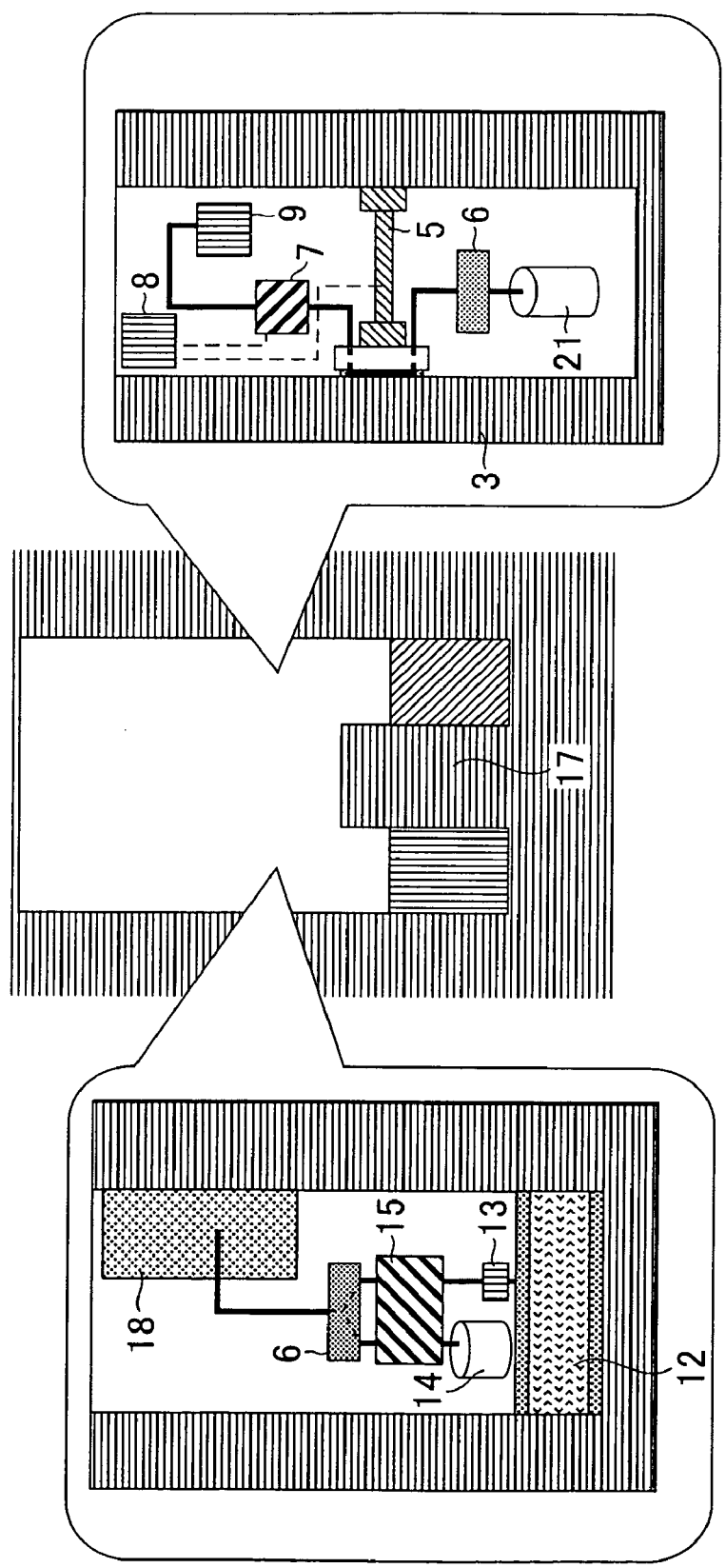
FIG. 6 is a schematic view showing the construction of a subterranean environment evaluating apparatus according to a second embodiment of the present invention.

FIG. 6 is a schematic view showing the construction of a subterranean environment evaluating apparatus according to a second embodiment of the present invention. In this second embodiment, a projection 17 is formed to project from a rock bed into a bored pit or a space for a subterranean laboratory facility. Onto a left side surface of the rock projection 17, a container 18 is mounted with its one side defined by the left side surface of the projection 17. Onto a right side surface of the rock projection 17, the geologic evaluation sensor used in the first embodiment is mounted using a pressure applying device 5, and water 21 (pure water or groundwater) is fed to a reaction cell 4 serving also as a channel by a liquid feed pump 6. The other construction is the same as that of the subterranean environment evaluating apparatus of the first embodiment. Thus, in this second embodiment, a geologic evaluation sensor 20 supplied with water is mounted to one side of the rock projection 17, and the container 18 for supplying a tracer 14 is mounted to the other side of the rock projection 17.

The groundwater mixed with the tracer 14 is fed to the container 18 in FIG. 6. A tracer solution diffuses through the rock projection 17 from the container 18, which is in contact with the left side surface of the rock projection 17, in a direction from the left to the right. Finally, the tracer solution seeps to the right side surface of the rock projection 17. The tracer having thus seeped is mixed in the water 21 fed to the reaction cell 4 serving also as the channel. The water mixed with the tracer in the reaction cell 4 serving also as the channel is measured for a tracer concentration in the same manner as in the subterranean environment evaluating of the first embodiment.

From the measured result, a PC 8 determines a breakthrough curve. Comparing tracer concentrations at an inlet and an outlet of the geologic evaluation sensor 20, the tracer concentration at an inlet is close to 0. A change of concentration ratio is therefore amplified to a larger value. The diffusion coefficient of the rock bed and the distribution coefficient between the rock bed and nuclide are measured from the breakthrough curve.

Generally, the amount of the tracer solution diffusing through the rock bed is very small, and therefore a tracer concentrations measuring method with high sensitivity is required. According to this embodiment, since the geologic evaluation sensor for measuring the tracer concentration is mounted to the rock projection 17, a very small amount of the tracer solution diffusing through the rock projection 17 from one side to the opposite side is applied to the geologic evaluation sensor, and therefore highly sensitive measurement can be realized.

Figure 7:
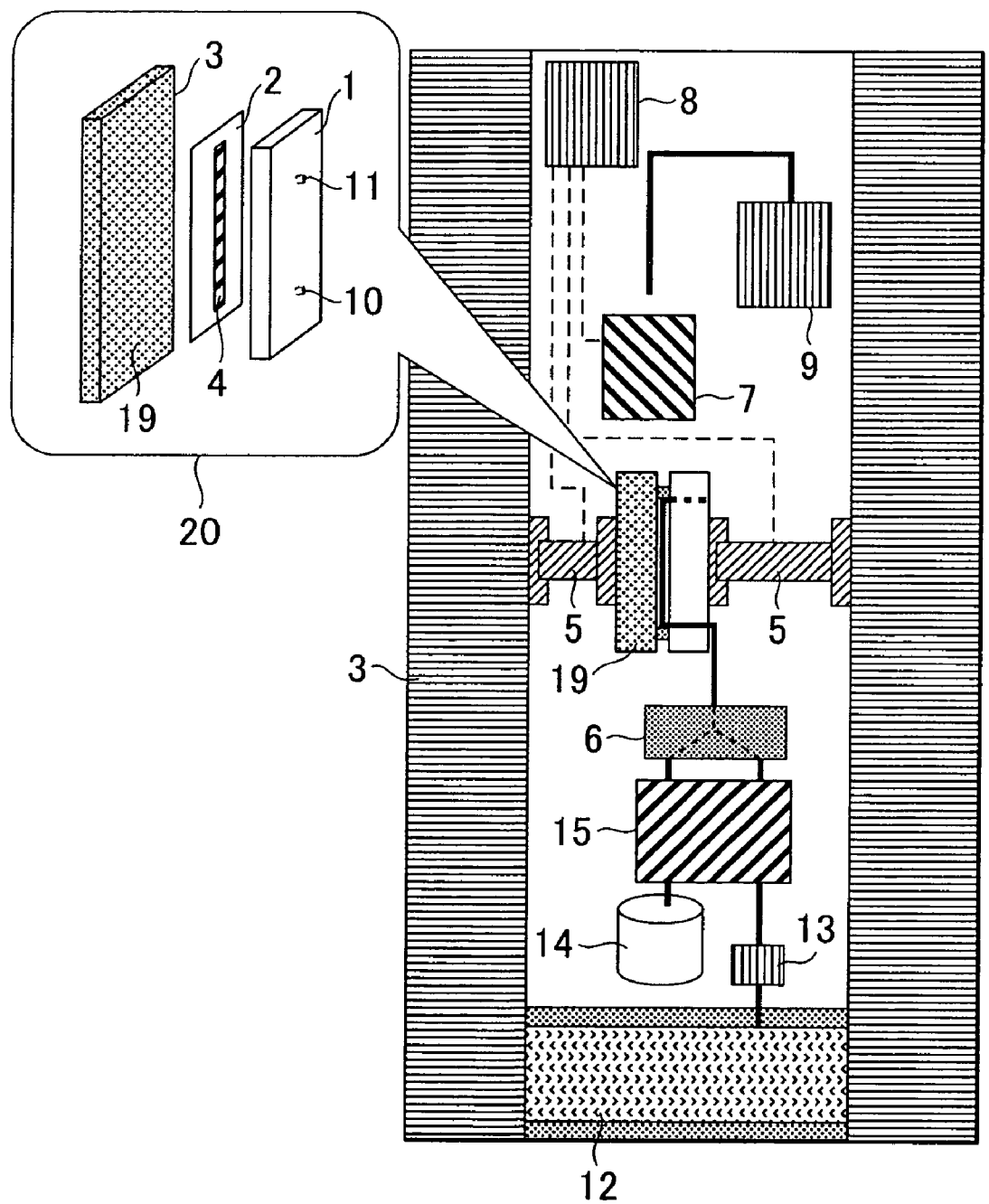
FIG. 7 is a schematic view showing the construction of a subterranean environment evaluating apparatus according to a third embodiment of the present invention.

The construction of a subterranean environment evaluating apparatus according to a third embodiment of the present invention will be described below with reference to FIG. 7. The construction of the subterranean environment evaluating apparatus of this second embodiment is basically the same as that of the first embodiment except that a reference sample 19 is taken into the pit from on the ground instead of using the specimen 3. With the subterranean environment evaluating apparatus of this third embodiment, the diffusion coefficient and the distribution coefficient under the environments of a pit formed underground by boring from on the ground or a shallow hole formed in a rock bed defining a space for a subterranean laboratory facility by using the reference sample 19. As a result, it is possible to evaluate influences upon the diffusion coefficient and the distribution coefficient due to the difference between a standard rock used on the ground and a subterranean rock.

A subterranean environment evaluating apparatus according to a fourth embodiment of the present invention differs from the apparatus according to the first embodiment in that the groundwater stored in the groundwater pool 12 is replaced with quasi-groundwater taken from on the ground. With the subterranean environment evaluating apparatus of this fourth embodiment, the diffusion coefficient and the distribution coefficient under the environments of a pit formed underground by boring from on the ground or a shallow hole formed in a rock bed defining a space for a subterranean laboratory facility by using the quasi-groundwater. As a result, it is possible to evaluate influences upon the diffusion coefficient and the distribution coefficient due to the difference between the quasi-groundwater used on the ground and the groundwater in subterranean environments with respect to the same rock sample.

What is claimed is:

1. A subterranean environment evaluating apparatus for measuring a diffusion coefficient of rock and a distribution coefficient between rock and groundwater by using the groundwater and a rock bed in subterranean environments, the apparatus comprising:
    a thin layer channel formed in a subterranean structure for allowing the groundwater to pass through said thin layer channel; and
    a concentration analyzer for measuring a concentration change of groundwater composition between an inlet and an outlet of said thin layer channel when the groundwater is caused to pass through said thin layer channel.

2. The subterranean environment evaluating apparatus according to claim 1, wherein said thin layer channel is constituted as a three-layered geologic evaluation sensor comprising a board chip having an inlet and an outlet for a solution, a gasket made of an elastic material and having a slit formed therein to provide a part of a reaction channel in the form of a reaction cell serving also as a channel, and a specimen as a measurement target.

3. The subterranean environment evaluating apparatus according to claim 2, further comprising pressurizing means for pressurizing the three layers of said geologic evaluation sensor.

4. The subterranean environment evaluating apparatus according to claim 2, wherein said specimen is a reference specimen taken from on the ground, and/or the groundwater is quasi-groundwater taken from on the ground.

5. The subterranean environment evaluating apparatus according to claim 1, wherein said thin layer channel is constituted using a rock bed surface of said subterranean structure.

6. A subterranean environment evaluating apparatus for measuring a diffusion coefficient of rock and a distribution coefficient between rock and groundwater by using the groundwater and a rock bed in subterranean environments, the apparatus comprising:
    a thin layer channel formed in a subterranean structure for allowing the groundwater to pass through said thin layer channel, said thin layer channel being constituted as a geologic evaluation sensor of a pressurized three-layered structure comprising a specimen formed by a rock bed surface as a target in said subterranean structure, a gasket made of an elastic material and having a slit formed therein to provide a part of a reaction cell serving also as a channel, and a board chip having an inlet and an outlet for a solution;
    a tracer unit for supplying a solution prepared by mixing a tracer in the groundwater to the inlet of said board chip;
    a concentration analyzer for measuring a change of tracer concentration of the solution discharged from the outlet of said board chip; and
    a processing unit for determining a breakthrough curve from a change rate of tracer concentration between the inlet and the outlet of said board chip, thereby calculating the diffusion coefficient and the distribution coefficient.

7. A subterranean environment evaluating apparatus for measuring a diffusion coefficient of rock and a distribution coefficient between rock and groundwater by using the groundwater and a rock bed in subterranean environments, the apparatus comprising:
    a rock projection left at the bottom of a subterranean structure;

a geologic evaluation sensor of a three-layered structure comprising a specimen provided as said rock projection, a gasket having a slit formed therein to provide a part of a reaction cell serving also as a channel, and a board chip having an inlet and an outlet, said geologic evaluation sensor being disposed on one side of said rock projection; and a container containing a solution prepared by mixing a tracer in the groundwater and having one side defined by said rock projection, said container being disposed on the other side of said rock projection, said geologic evaluation sensor measuring the solution diffusing from said container through said rock projection, thereby determining the diffusion coefficient and the distribution coefficient from a measured concentration change of the solution.

8. A subterranean environment evaluating method for measuring a diffusion coefficient of rock and a distribution coefficient between rock and groundwater by using the groundwater and a rock bed in subterranean environments, the method comprising the steps of:

causing the groundwater to flow through a thin layer channel formed by using a rock bed surface as a part of said thin layer channel;

measuring a concentration change of groundwater composition between an inlet and an outlet of said thin layer channel to obtain a breakthrough curve; and determining the diffusion coefficient and the distribution coefficient based on the breakthrough curve.

9. The subterranean environment evaluating method according to claim 8, further comprising the steps of:

mixing a tracer in the groundwater; and measuring a change of tracer concentration between the inlet and the outlet of said thin layer channel.

* * * * *